United States Patent

Harada et al.

[19]

[11] Patent Number: 4,485,812
[45] Date of Patent: Dec. 4, 1984

[54] HIGH FREQUENCY INCISING DEVICE

[75] Inventors: Shinichi Harada, Tsurugashima; Katsuhiko Furuya, Wako; Kazukiyo Tamada, Kawaguchi, all of Japan

[73] Assignee: Kabushiki Kaisha Medos Kenkyusho, Japan

[21] Appl. No.: 448,781

[22] Filed: Dec. 10, 1982

[30] Foreign Application Priority Data

Dec. 11, 1981 [JP] Japan .............................. 56-184836[U]

[51] Int. Cl.³ ............................................. A61B 17/39
[52] U.S. Cl. ................................................ 128/303.15
[58] Field of Search ...................... 128/303.13, 303.14, 128/303.15, 303.17

[56] References Cited

U.S. PATENT DOCUMENTS 3,910,279 10/1975 Okada et al. ................... 128/303.15
4,181,131 1/1980 Ogiu .................................. 128/303.15
4,325,374 4/1982 Komiya ............................. 128/303.15

*Primary Examiner*—Lee S. Cohen
*Assistant Examiner*—Steven Falk
*Attorney, Agent, or Firm*—Steinberg & Raskin

[57] ABSTRACT

The high frequency incising device includes a flexible tubular member secured to a manipulating unit. The tubular member has an open ended tip portion and a pair of longitudinal spaced openings in the wall of the tube. An electrically conductive wire extends through the flexible tube passing outwardly thereof through a forward one of the longitudinal openings and being anchored to the flexible tube at a rearward one of the longitudinal openings. Such anchoring is accomplished by bending the wire toward the tip portion of the tube. A second bend portion in the outwardly exposed wire is directed away from the tip portion such that the outwardly exposed wire takes on the shape of a fan or sector. An opposite end of the wire is connected to an electrically conductive pipe that is movably disposed in the manipulating unit and the tube. An end of the movable pipe that projects beyond the manipulating unit is connected to an anchoring device that is movable with respect to the manipulating unit. Accordingly movement of the anchoring device causes movement of the electrically conductive wire which causes the outwardly exposed portion of the wire to bulge away from the tube in an amount that is based upon a relative position of the anchoring device with respect to the manipulating unit. A contrast medium that is injected into the tube has a relatively unobstructed passage through the tip of the tube since the wire disposed within the tube and the bent portions of the wire within the tube do not impede flow of such contrast medium to the tip.

12 Claims, 5 Drawing Figures

HIGH FREQUENCY INCISING DEVICE

BACKGROUND OF THE INVENTION

This invention relates to a high frequency incising device for incision of the Vater's papilla within the duodenum and, more particularly, to an incising device with a stabilized electrically conductive wire that does not deviate from a desired direction of incision.

Devices for incising the Vater's papilla are usually introduced through the forceps channel of an endoscope into the body cavity by direct observation through the endoscope in accordance with a method of surgical papillary incision characterized as endoscopic papillectomy.

This surgical method is used for choledocholithiasis or benign papillary constriction, in which the sphincter muscle of duodenum Vater's papilla into which the common bile duct opens is endoscopically incised to enlarge the opening thereof so that stones produced within the common bile duct may be spontaneously discharged or seized and picked out by a litholabe introduced through the incision into the common bile duct.

The incising device conventionally used for this papillectomy typically comprises a flexible tube introduced into the forceps channel of the endoscope and provided adjacent its tip with a pair of longitudinally spaced through holes. One end of an electrically conductive wire is anchored to the tip of the tube by a metallic pipe. A portion of the wire is exposed outside the tube between the pair of through holes, and a manipulator unit is provided at a rear end of the tube, wherein an opposite end of the wire is connected such that operation of the manipulator unit controls protrusion or retraction of the wire through the rear through hole.

One known type of incising device is generally classified as the push type wherein the wire is caused to bulge out laterally from the tube between the pair of through holes in a semicircular form as the wire is pushed forward within the tube. Another known type of prior art incising device is generally classified as the pull type in which the tube is forcibly curved between the pair of through holes to cause the exposed wire to define a chord of semicircular form.

In both categories of the known incising devices a sufficient quantity of contrast medium is injected through an inlet at the rear end of the tube into the common bile duct. The contrast medium is used to confirm whether the tip of the incising device has been correctly inserted into the common bile duct on the basis of an image contrast provided by an X-ray taken before the actual incision is carried out using high frequency current. A highly skillful manipulation of the known devices is required to achieve an incision of the proper depth, since an incision that is too deep may cause profuse bleeding which can lead to other problems, and an incision that is too small will prevent adequate removal of stones.

It is thus desirable to provide an incising device that can be easily controlled to provide an accurate incision of Vater's papilla.

SUMMARY OF THE INVENTION

Accordingly it is an object of the invention to provide an improved, long lasting, high frequency incising device which permits an accurately directed incising operation and easy adjustment of the amount of incision so that an optimum incision can be obtained.

A further object of the invention is to provide a high frequency incising device that does not obstruct the passage of a contrast medium to the common bile duct.

In accordance with the present invention, the high frequency incising device includes an elongated flexible tube secured to a manipulator unit at one end thereof and having an open ended tip portion at the opposite end thereof. An electrically conductive wire extends through the flexible tube, and outwardly thereof through a pair of longitudinal spaced openings in the wall of the tube. One end of the electrically conductive wire is anchored to the tube at a rearward one of the spaced openings with respect to the tip of the tube by a bent portion that is directed toward the tip. A portion of the outwardly exposed wire that extends from a forward one of the spaced openings with respect to the tip of the tube includes a bend directed away from the tip such that the outwardly exposed wire is in the shape of a fan or sector.

The wire is connected to a movable member such as an electrically conductive pipe or tube that projects beyond the manipulator member for securement to an anchoring means that is movable with respect to the manipulator member. The electrically conductive wire is thus movable relative to the tube upon movement of the anchoring means relative to the manipulator unit. Accordingly the amount by which the exposed electrical wire bulges away from the tube corresponds to the relative position of the anchoring means with respect to the manipulator unit.

In a further embodiment of the invention, a coating of insulation material is provided on the electrically exposed wires between the bent portions. Other features and advantages of the invention will be apparent from the following description.

DESCRIPTION OF THE DRAWINGS

A more complete appreciation of the present invention and many of the attendant advantages thereof will be readily understood by reference to the following detailed description when considered in connection with the accompanying drawings in which.

DESCRIPTION OF THE PREFERRED EMBODIMENTS

Figure 1:
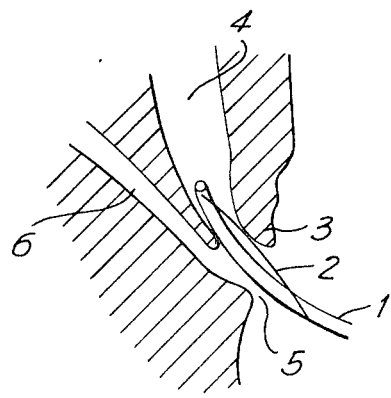
FIGS. 1 and 2 are simplified schematic views showing prior art incising devices of the push type and the pull type, respectively, during performance of an incising operation.

Referring now to the drawings wherein like reference characters designate identical or corresponding parts throughout the several views, and more particularly to FIG. 1, a known incising device of the push type comprises a flexible tube 1 containing an electrically conductive wire 2. The wire 2 is partially exposed outside the flexible tube 1 so as to engage against the papillary sphincter 3 after the tube is directed into the common bile duct 4 from Vater's papilla 5. The pancreatic duct 6 also communicates with Vater's papilla 5.

The partially exposed conductive wire 2 is thus placed to extend over a part of the papillary sphincter which is to be incised. During such incision the tube 1 is held stationary and the wire 2 is progressively forced in a known manner to bulge outwardly of the tube 1 while being supplied with a high frequency current to thereby accomplish the desired incision.

However, various problems have been encountered with the prior art devices. For example, the wire 2 must be made of a flexible fine material and must also be forced to assume a generally semicircular shape. Furthermore, the exposed part of the wire 2 must be inserted into the common bile duct, a matter of some difficulty since the opening of Vater's papilla is relatively small. Thus the exposed portion of the wire 2 that bulges away from the tube 1 is easily deflectable and readily bent by the resistance of the body tissue that is to be incised. Consequently the desired direction of incision is difficult to maintain and the wire 2 is easily broken.

Another problem is the difficulty encountered in manipulating the incising device to control the precise amount of wire that is bulged out of the tube 1 in order to precisely control the depth of incision. Accordingly only a highly skilled person can operate the push type incising device to achieve a desired incision to the appropriate depth.

Figure 2:
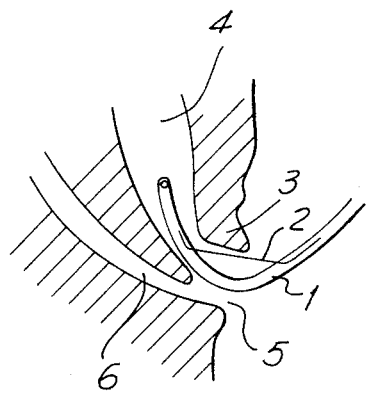

FIG. 2 shows a known incising device of the pull type. This device also includes a flexible tube 1 containing an electrically conductive wire 2 partially exposed outside the tube 1 to engage the papillary sphincter 3 as previously described. Unfortunately this prior art device has various problems, some of which are similar to those of the push type incising device. One such problem is the requirement of the flexible fine wire 2 since pulling of the wire 2 often causes the tube 1 to buckle thereby resulting in an incision that is too deep. A further problem is that the exposed part of the wire 2 must be inserted into the common bile duct 4. Therefore the desired direction of incision is often deviated from, and the wire 2 is easily broken.

Figure 4:
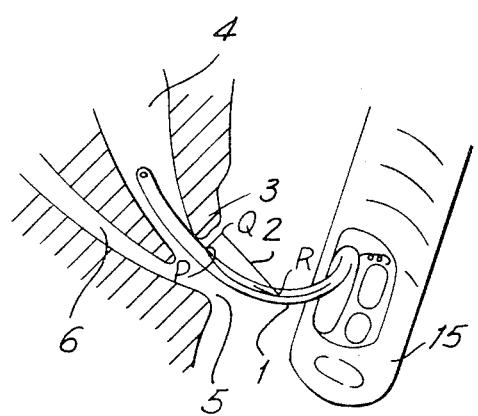
FIG. 4 is a simplified schematic view thereof during performance of an incising operation; and, FIG. 5 is a sectional view of an incising device incorporating another embodiment of the present invention.
Figure 3:
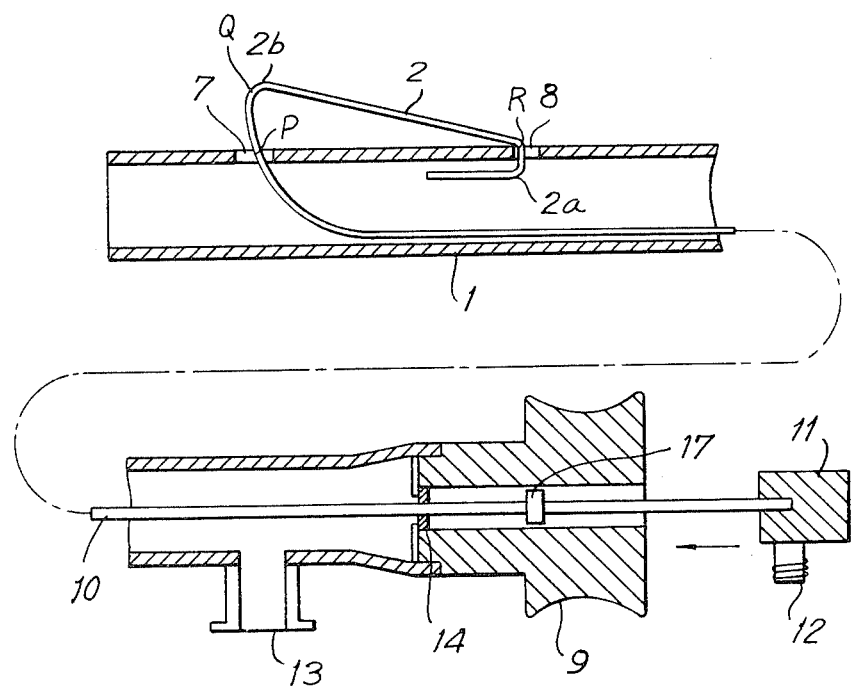
FIG. 3 is a sectional view of an incising device incorporating one embodiment of the present invention.

Referring to FIG. 3, a tube 1 is electrically insulated and sufficiently flexible and fine to be inserted through a forceps channel of an endoscope 15 as shown schematically in FIG. 4. The tube 1 has a tip portion which is open and a wall portion having two longitudinally spaced through openings 7 and 8 adjacent the tip. The openings 7 and 8 are spaced a predetermined distance from each other, the front opening 7 being closer to the tip than the rear opening 8. A rear end of the tube 1 is fixed to a non-conductive manipulator unit 9. The electrically conductive wire 2 which functions as the high frequency incising device is advanced and retracted in a controlled predetermined fashion with respect to the manipulator unit 9.

The wire 2 is movable through the tube 1 extending outwardly thereof through the opening 7, and bent at one end in a direction toward the tip of the tube 1 to form a bend 2a by which the wire 2 is anchored at R on an edge of the rear opening 8. Under this arrangement a part of the wire 2 extending between a point P at which the wire exists from the front opening 7 and the anchor point R at the rear opening 8 is exposed outside the tube 1, and this exposed part of the wire 2 is bent to form another bend 2b at a point Q outside and adjacent the front opening 7 at a point Q. Thus, as clearly seen in FIG. 3, the exposed part of the wire 2 is constituted by a wire portion PQ which extends from within tube 1 through the front opening 7 in a direction substantially transverse to the axis of tube 1 in the region of opening 7 and a wire portion QR which extends from portion PQ generally toward the rear end of tube 1 and which has an end region anchored at the rear opening 8.

An opposite end of the wire 2 is connected to a movable member comprising a relatively non-flexible electrically conductive tube or pipe 10. The pipe 10 is connected to an anchoring means 11 adapted to be advanced and retracted with respect to the manipulator unit 9. The opposite end of the wire 2 is also connected by an electric connection adapter 12 mounted on the anchoring means 11 to a high frequency voltage source.

A rear end portion of the tube 1 adjacent the manipulator unit 9 is provided with a contrast medium entry port 13. Sealing means 14 are provided at the junction of the tube 1 and the manipulator unit 9 to prevent any contrast medium from leaking around the rear end of the tube 1 even during advancement or retraction of the anchoring means 11 as well as the wire 2 and the pipe 10. Contrast medium may be discharged through the opening formed at the tip of the tube 1. If desired a guide or stop member 17 can be provided around the pipe 10 in the manipulator unit 9.

Displacement of the anchoring means 11 relative to the manipulator unit 9 so as to advance the wire 2 toward the tip of the tube 1 causes the wire 2 to be projected out of the front opening 7. The portion of the wire 2 thus exposed outside the tube 1 bulges outwardly in the shape of a fan or sector. The fan or sector shape of the exposed portion of the wire 2 which bulges away from the tube 1 can be accurately adjusted in accordance with the displacement of the anchoring means 11. Consequently a given position of the anchoring means 11 relative to the manipulator unit 9 corresponds to a predetermined height or bulging away of the exposed part of the wire 2, and more specifically, the displacement of the anchoring means determines the length of the portion PQ of wire 2.

FIG. 4 schematically shows the incising device of the present invention introduced from the tip of the endoscope 15 which has been introduced into the duodenum into the common bile duct 4. Thus the tip of the tube 1 is introduced through the forceps-channel of the endoscope 15 into the Vater's papilla 5 under direct observation through the endoscope. Since both the pancreatic duct 6 and the common bile duct 4 merge into the Vater's papilla, it can be confirmed using X-rays or other appropriate visual aid, that the tip of the tube 1 is introduced into the common bile duct 4 rather than the pancreatic duct 6. Such confirmation can be made according to an image contrast formed by contrast medium injected through the tube 1 into the common bile duct 4 from the entry port 13.

To facilitate such operation, it is preferred to select a relatively long tube length between the tube tip and the front opening 7 along which no part of the wire is exposed outside tube 1. Appropriate control of the manipulator unit 9 will cause the tube 1 to be progressively forced into the common bile duct 4 while the desired amount of bulge of the exposed portion of the wire 2 is adjusted. A high frequency current is then transmitted through the wire 2. Thus, as seen in FIG. 4, the bulged out portion of the wire 2, i.e., the portion PQ of the wire 2 extending between the bend 2b and the part of the wire 2 lying closely adjacent the front opening 7, incises the papillary sphincter 3 and thereby enlarges the opening of the common bile duct 4.

The tube 1 employed in the present invention is relatively fine and made of a material such as fluorocarbon polymer that is capable of being bent without detrimental effect. The wire 2 or wire rod may be thicker than those employed by the prior art devices since it is unnecessary to introduce any part of the wire 2 that is exposed outside the tube 1 through the Vater's papilla into the common bile duct together with the tube itself, as has been a requirement of the prior art devices.

A further advantage of the present invention is that the distance between the longitudinal spaced openings 7 and 8 in the tube 1 adjacent its tip can be reduced in comparison to the spacing between such openings in the prior art devices, because the exposed portion of the wire 2 bulges outwardly of the tube in the form of a fan shape or a sector shape and the bend 2b of the wire 2 lies entirely within the bulged out extent of the exposed wire 2. As a result, the bulged out wire portion has sufficient strength to avoid the bending problems that occur in the prior art devices wherein the exposed wire is forceably bent by the resistance of the body tissue engaged by the wire during incision. The novel shape of the exposed wire portion of the present invention has less tendency to deflect sideways as do the prior art devices in response to the resistance of the body tissue during the incising operation. A further feature of the present invention is that the amount of controlled displacement at the manipulator unit 9 substantially corresponds to the amount by which the exposed part of the wire 2 bulges outwardly from the tube 1. Accordingly the incision depth can be progressively increased under direct observation of the part being incised. The control afforded by the incising device permits the desired incision to be achieved with the greatest amount of safety without the necessity of any particular skill and experience. The incising device of the present invention also has less tendency than the prior art devices to deviate or deflect sideways from the desired direction of incision.

The present invention provides still another advantage with respect to the manner in which the wire is anchored within the tube. In the prior art devices, the wire is anchored within a metallic pipe that is anchored within the tube adjacent the tip thereof. This arrangement of the metallic pipe obstructs the flow of a contrast medium through the tube when the contrast medium is injected therein. There is substantially less impedance to the flow of contrast medium when it is injected in the incising device of the present invention since the anchoring effect is obtained by bending the wire at the location 2a around the edge of the rear through opening 8. This turning back of wire toward the tip allows a smooth flow of contrast medium that is injected into the contrast medium injection passage 13.

Figure 5:
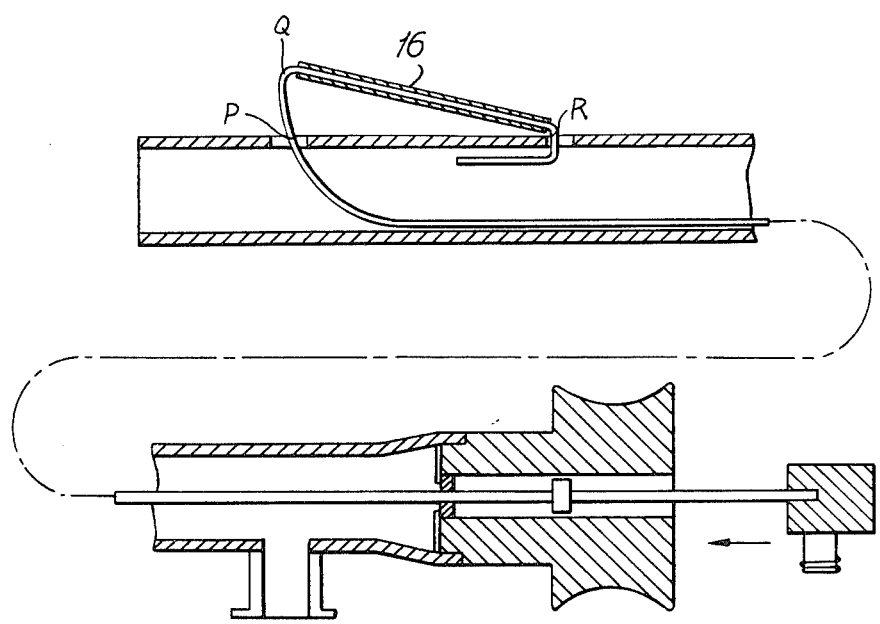

In another embodiment of the invention as shown in FIG. 5 the exposed part QR of the wire 2 is coated with thermal insulating material 16. Thus if the insulated portion of the wire 2 comes in contact with a part of the body cavity other than the region being incised there is no danger of burning or otherwise injuring this part of the body. Thus the incision can be achieved with substantial safety. Accordingly an important feature of the present invention is that the actual incising edge is the portion PQ of exposed wire that extends between the front opening 7 of the tube 1 and the bend 2b of the exposed wire 2. As seen in FIGS. 3-5, incising portion PQ of wire 2 extends from the opening 7 in a direction substantially transverse to the axis of tube 1 in the region of opening 7.

In order to obtain accurate incision of the papillary sphincter 3 it is necessary that the portion of electrically conductive wire between the bends 2b and 2a have sufficient rigidity when it is bulged outwardly by pushing the wire 2. Such rigidity is based on the thickness of the wire 2 and is enhanced with the coating of insulating material, and by making the distance between the front opening 7 and the rear opening 8 as short as possible. Also the bending at the bent portion 2b is preferably sharp rather than a continuous curve.

What is claimed is:

1. A high frequency incising device for use with an endoscope, comprising a flexible tube having a wall portion, a forward tip and a rearward end, a pair of longitudinally spaced openings in said wall portion including a rear opening and a front opening which is closer to said tip of said flexible tube than is said rear opening, an electrically conductive wire in said tube and a part of said wire exposed outside said tube, said exposed wire part including a first incising wire portion which extends from within said tube through said front opening in a direction substantially transverse to the axial direction of said tube in the region of said front opening and a second wire portion integral with and extending from said first incising wire portion generally toward said rearward tube end, said second wire portion having an end region constituting a first end region of said electrically conductive wire anchored at said rear opening, said device further including a movable member extending through the tube for longitudinal movement in opposite directions with respect to said tube, said wire having a second end region opposite from said first end region, said second wire end region being connected to the movable member such that the length of said first incising wire portion is determined by the position of said movable member, and means for electrically connecting said conductive wire with an electrical supply.

2. The high frequency incising device according to claim 1, wherein said movable member is a non-flexible member having a first end portion inside said flexible tube affixed to said second end region of said wire and a second end portion projecting outside said tube.

3. The high frequency incising device according to claim 2, wherein said means for electrically connecting comprises said non-flexible member being electrically conductive and means provided at the second end portion of said non-flexible member for connection with an electrical supply.

4. The high frequency incising device according to claim 2, including means for manipulating said flexible tube connected to an end of said flexible tube opposite said tip, said manipulating means including means for guiding movement of said non-flexible member in said flexible tube.

5. The high frequency incising device according to claim 1, including means on said flexible tube for permitting introduction into said tube of an injectible contrast medium.

6. The high frequency incising device of claim 1 wherein said end region of said second wire portion of said exposed wire part has a first bend formed therein anchoring said end region at said rear opening and wherein said first incising and second wire portions of said exposed wire part are integrally joined at a second sharp bend formed in said exposed wire part.

7. The high frequency incising device according to claim 6, wherein said first incising wire portion comprises a substantially curved portion extending from a point inwardly of said flexible tube to said second sharp bend.

8. The high frequency incising device according to claim 6, wherein said second wire portion comprises a substantially straight portion extending from said second sharp bend to said first bend.

9. The high frequency incising device according to claim 8, wherein said first incising wire portion comprises a substantially curved portion extending from a point inwardly of said flexible tube to said second sharp bend.

10. The high frequency incising device according to claim 9, wherein insulating means are provided around said second wire portion.

11. The high frequency incising device according to claim 1, wherein the distance between said longitudinally spaced openings is selected such that the length of said second wire portion is sufficiently small to prevent buckling of said second wire portion when a predetermined force is imposed on said first incising wire portion.

12. The high frequency incising device according to claim 1, wherein insulating means are provided around said second wire portion.

* * * * *